(12) United States Patent
Han et al.

(10) Patent No.: US 10,344,317 B2
(45) Date of Patent: Jul. 9, 2019

(54) METHOD AND A SEQUENCE COMBINATION FOR PRODUCING NUCLEIC ACID FRAGMENTS

(71) Applicant: BGI SHENZHEN CO., LIMITED, Shenzhen (CN)

(72) Inventors: Hongyan Han, Shenzhen (CN); Chunyu Geng, Shenzhen (CN); Guanying Guo, Shenzhen (CN); Wenwei Zhang, Shenzhen (CN); Hui Jiang, Shenzhen (CN); Yuan Jiang, Shenzhen (CN)

(73) Assignee: MGI TECH CO., LTD, Shenzhen, Guangdong (CN)

( * ) Notice: Subject to any disclaimer, the term of this patent is extended or adjusted under 35 U.S.C. 154(b) by 133 days.

(21) Appl. No.: 15/518,760

(22) PCT Filed: Oct. 13, 2014

(86) PCT No.: PCT/CN2014/088509
§ 371 (c)(1),
(2) Date: Apr. 12, 2017

(87) PCT Pub. No.: WO2016/058121
PCT Pub. Date: Apr. 21, 2016

(65) Prior Publication Data
US 2018/0251813 A1    Sep. 6, 2018

(51) Int. Cl.
*C12P 19/34*        (2006.01)
*C12Q 1/6806*       (2018.01)
(Continued)

(52) U.S. Cl.
CPC ......... *C12Q 1/6806* (2013.01); *C12Q 1/6855* (2013.01); *C12Q 1/686* (2013.01);
(Continued)

(58) Field of Classification Search
None
See application file for complete search history.

(56) References Cited

U.S. PATENT DOCUMENTS 6,828,098 B2 * 12/2004 Langmore .............. C12N 15/10
                                                      435/6.1
2004/0185484 A1    9/2004 Costa et al.
(Continued)

FOREIGN PATENT DOCUMENTS

CN    101278058 A    10/2008
CN    102296065 A    12/2011
(Continued)

OTHER PUBLICATIONS

Written Opinion of the International Searching Authority for PCT/CN2014/088509 dated Jul. 17, 2015, and its official English translation from WIPO.
(Continued)

*Primary Examiner* — Kenneth R Horlick
(74) *Attorney, Agent, or Firm* — Ladas & Parry, LLP

(57) ABSTRACT

Disclosed are a nucleic acid fragmentation method and a sequence combination. The method comprises the following steps: subjecting a denatured nucleic acid to annealing and an extension reaction by using a single-stranded 5'-end extension primer, wherein the single-stranded 5'-end extension primer comprises a sequencing platform adaptor sequence of a 5' end and a connected random sequence, and the random sequence is subjected to annealing on a random site of the denatured nucleic acid; and directionally connecting a double-stranded 3'-end adaptor sequence to the 3' end of the nucleic acid generated in the extension reaction, and carrying out denaturalization and purification to obtain a
(Continued)

fragmented single-stranded nucleic acid with adaptor sequences on two ends.

18 Claims, 6 Drawing Sheets

Specification includes a Sequence Listing.

(51) Int. Cl.
*C12Q 1/6855* (2018.01)
*C12Q 1/686* (2018.01)

(52) U.S. Cl.
CPC . *C12Q 2525/179* (2013.01); *C12Q 2525/191* (2013.01); *C12Q 2535/122* (2013.01)

(56) References Cited

U.S. PATENT DOCUMENTS

| | | |
|---|---|---|
| 2009/0142758 A1 | 6/2009 | van Eijk et al. |
| 2014/0213485 A1 | 7/2014 | Weissman |
| 2014/0249038 A1 | 9/2014 | Jiang et al. |
| 2017/0275616 A1* | 9/2017 | Geng ................ C12Q 1/68 |

FOREIGN PATENT DOCUMENTS

| | | |
|---|---|---|
| CN | 102329876 A | 1/2012 |
| CN | 102373288 A | 3/2012 |
| CN | 102485979 A | 6/2012 |
| EP | 2 749 653 A1 | 7/2014 |
| WO | 2004/081225 A2 | 9/2004 |
| WO | 2009/032167 A1 | 3/2009 |
| WO | 2013/055955 A1 | 4/2013 |
| WO | 2013/191775 A2 | 12/2013 |

OTHER PUBLICATIONS

International Preliminary Report on Patentability (Chapter I) for PCT/CN2014/088509 dated Apr. 18, 2017, and its official English translation from WIPO.

Extended European Search Report for EP application No. 14904045.3, dated Feb. 21, 2018.

International Search Report for PCT/CN2014/088509 dated Jul. 15, 2015 and its English translation provided by WIPO.

Written Opinion of the International Search Authority for PCT/CN2014/088509 dated Jul. 17, 2015 and its English translation provided by WIPO.

* cited by examiner

METHOD AND A SEQUENCE COMBINATION FOR PRODUCING NUCLEIC ACID FRAGMENTS

CROSS REFERENCE TO RELATED APPLICATION

The present application is the U.S. national phase of PCT Application PCT/CN2014/088509 filed on Oct. 13, 2014, the disclosure of which is incorporated herein by reference in its entirety.

TECHNICAL FIELD

The present invention relates to the field of molecular biology, particularly to a nucleic acid fragmentation method and a sequence combination.

BACKGROUND OF THE INVENTION

Ever since Frederick Sanger determined genomic sequence for the first time, DNA sequencing technologies have been developing fast over more than 30 years, and three generations of DNA sequencing technologies with distinct characteristics evolved over time. Among them, the second generation sequencing (or, next generation sequencing, abbreviated as NGS) technology is mainly characterized by highly increased throughput, remarkably reduced cost and greatly shortened cycle and is thus widely used in life science basic theory research and bio-industry applications.

The $21^{st}$ century sees tremendous changes in the technologies of DNA sequencing, predominantly characterized by a sharp increase in sequencing throughput (sequencing data size) and a drastic decrease in the sequencing cost for each base in the raw data. The second generation sequencing technology, particularly represented by Roche, Illumina and Life Technologies, occupies most of the sequencing market thanks to sequencing by ligation or sequencing by synthesis, including pyrosequencing and reversible chain termination. Commercially available instruments from the three companies deliver several Gbp of DNA sequence per week in the form of short contiguous fragments or reads, resulting in the cost of sequencing being greatly decreased in comparison with that of the first generation sequencing technology.

With the ongoing development of sequencing technologies, the trend of development of the sequencing industry can be summarized to be higher throughput, higher accuracy and lower cost. Rapid advancement will certainly be achieved in the former two aspects with the development of technologies, while the cost of sequencing is still considerably higher than people's expectation of detecting human whole genome for 1000 US dollars (30×, about 10 US dollars per Gb), despite the annual drop in sequencing cost as technologies progress. Therefore, the step of sample library preparation on the upstream of the sequencing process would be a key factor in further greatly decreasing sequencing cost, and represents the main technological direction in further development of sequencing technologies.

The basic principle underlying NGS library construction involves randomly breaking DNA or RNA of interest into small fragments and ligating adaptor sequences suitable for sequencing platforms. Generally, the following central steps are included: fragmenting DNA or RNA and selecting fragments having the desired sizes; converting the fragments into double-stranded DNA; ligating adaptor sequences suitable for sequencing platforms; and conducting quality inspection on the resulting library. Library size is one of the most critical technical indexes in NGS library construction.

In general, there are mainly two types of methods used in NGS library fragmentation: physical method and enzymatic method.

The physical method mainly involves a Covaris disruptor based on proprietary Adaptive Focused Acoustics (AFA) technology, whereby geometrically focused acoustic energy is utilized under isothermal condition. Acoustic energy having a wavelength of 1 mm is focused to a sample by a spherical solid-state ultrasonic transducer of >400kHz. The method ensures the maintenance of the completeness of nucleic acid samples and achieves a high recovery rate. The Covaris disruptor includes the economical M series, the single-tube full-power S series and the higher throughput E and L series. The fragments obtained from the physical method exhibit a good fragment randomness. However, a number of Covaris disruptors are needed for the sake of throughput, and subsequent separate operations of terminal processing, adaptor ligation, PCR and various purifications are also required. Additionally, consumables associated with the Covaris disruptor need to be used, leaving only limited room for cost reduction.

The enzymatic method mainly involves NEB Next dsDNA Fragmentase available from NEB, or transposase from Nextera kit available from Epicentra (already purchased by Illumina). The former first utilizes DNase I to introduce random nicks into double-stranded DNA, then utilizes Fragmentase to recognize the nick positions to cleave the complementary DNA strands, thus achieving the aim of breaking the DNA. Such a reagent can be used in genome DNA, whole genome amplification products, PCR products etc. and provides good randomness. Nevertheless, it will generate some artificial short fragment insertions and deletions, and also inevitably entails subsequent separate operations of terminal processing, adaptor ligation, PCR and corresponding purifications. The latter, utilizing transposase, can achieve double-stranded DNA fragmentation and adaptor ligation at the same time, thus reducing the length of time for sample processing. However, the transposase embedded in the target sequence may inhibit subsequent enzymatic reactions, and possible purification steps would undoubtedly increase the cost and the time of library construction.

SUMMARY OF THE INVENTION

The present invention provides a nucleic acid fragmentation method and a sequence combination. The method can effectively achieve random breaking of a nucleic acid sample without the need of large-scale apparatus and equipment, having the advantages of being simple, convenient, fast, low-cost and highly automatic.

In the first aspect of the present invention, it provides a nucleic acid fragmentation method, comprising the following steps:

subjecting a single-stranded 5'-end extension primer to anneal to a denatured nucleic acid and to have an extension reaction, wherein the single-stranded 5'-end extension primer comprises a sequencing platform adaptor sequence at the 5'-end and a random sequence linked thereto, and the random sequence is to be subjected to anneal to a random site of the denatured nucleic acid; and directionally ligating a double-stranded 3'-end adaptor sequence to the 3'-end of the nucleic acid generated in the extension reaction, following denaturation and purification, fragmented single-stranded nucleic acid comprising an adaptor sequence at both terminal ends generate.

In a preferred embodiment of the present invention, after ligating the double-stranded 3'-end adaptor sequence, primer-specific PCR amplification is conducted to generate double-stranded nucleic acid products comprising an adaptor sequence at both terminal ends.

In a preferred embodiment of the present invention, the random sequence has a length of 3 to 12 nt, preferably 5 to 8 nt.

In a preferred embodiment of the present invention, the denaturation is alkali denaturation or thermal denaturation; preferably, the alkali denaturation is conducted by treatment with a NaOH or KOH solution; and preferably, the thermal denaturation is conducted at a temperature of 95° C. to 98° C.

In a preferred embodiment of the present invention, the 5'-end sequencing platform adaptor sequence and the double-stranded 3'-end adaptor sequence are selected from the adaptor sequences available for CG, Illumina or Ion Torrent sequencing platforms, preferably the adaptor sequences available for CG sequencing platform.

In a preferred embodiment of the present invention, in the annealing and extension reaction step of the method, at least one factor selected from the group consisting of the usage amount of the template nucleic acid, the concentration of the extension primer, the concentrations of dNTPs, the extension duration, the type and the usage amount of the polymerase is controlled to obtain suitable fragment lengths for a corresponding sequencing platform.

In a preferred embodiment of the present invention, the usage amount of the template nucleic acid is between 50 to 1000 ng.

In a preferred embodiment of the present invention, the extension duration is between 5 to 30 minutes.

In a preferred embodiment of the present invention, the polymerase is selected from the group consisting of Klenow Fragment, Taq DNA polymerase, phusion DNA polymerase or *E. coli* DNA polymerase I.

In a preferred embodiment of the present invention, the relationship between the usage amount of dNTPs and the usage amount of the template nucleic acid is as follows: the usage amount of dNTPs (nmol)=$2*10^{21}*m/Na*5$ to $2*10^{21}*m/Na*5000$, wherein Na represents Avogadro's number, and m represents the usage amount of the template nucleic acid in ng.

In a preferred embodiment of the present invention, the relationship between the usage amount of the extension primer and the usage amount of the template nucleic acid and the length of the extended fragment is as follows: the usage amount of the extension primer (pmol)=$2*10^{24}*m/(N*Na)*5$ to $2*10^{24}*m/(N*Na)*1024$; wherein Na represents Avogadro's number, m represents the usage amount of the template nucleic acid in ng, and N represents the length of the main band of the extended fragments.

In a preferred embodiment of the present invention, the 3'-end of each single strand of the double-stranded 3'-end adaptor sequence is a nucleotide with dideoxy modification.

In a preferred embodiment of the present invention, one of the primers used in the primer-specific PCR amplification comprises a sample tag sequence.

In the second aspect of the present invention, there is provided a sequences combination for nucleic acid fragmentation, the sequence combination comprising:

a single-stranded 5'-end extension primer, comprising a sequencing platform adaptor sequence at the 5'-end and a random sequence linked thereto, wherein the random sequence is to be subjected to anneal to a random site of a denatured nucleic acid and to an extension reaction; and a double-stranded 3'-end adaptor sequence, wherein the double-stranded 3'-end adaptor sequence is to be directionally ligated to the 3'-end of the nucleic acid generated in the extension reaction, following denaturation and purification, fragmented single-stranded nucleic acids comprising an adaptor sequence at both terminal ends generate.

In a preferred embodiment of the present invention, the sequence combination further comprises:

PCR primers that specifically bind to the terminal adaptor sequences, whereby primer-specific PCR amplification is conducted to generate double-stranded nucleic acid products comprising an adaptor sequence at both terminal ends.

In a preferred embodiment of the present invention, the random sequence has a length of 3 to 12 nt, preferably 5 to 8 nt.

In a preferred embodiment of the present invention, the 5'-end sequencing platform adaptor sequence and the double-stranded 3'-end adaptor sequence are selected from the adaptor sequences available for CG, Illumina or Ion Torrent sequencing platforms, preferably the adaptor sequences available for CG sequencing platform.

The nucleic acid fragmentation method of the present invention effectively achieves random amplification of a nucleic acid sample by random primer extension procedure, thus obtaining nucleic acid fragments similar to that would be obtained by a conventional disruption method. However, the method of the present invention does not need to use conventional large-scale apparatus and equipment, making it possible for medium and small-sized research institutes, colleges and universities and downstream application sectors to independently conduct high-throughput library preparation. Moreover, the method has the advantages of being simple, convenient, fast, low-cost and highly automatic, which greatly expands the application fields of large-scale high-throughput sequencing.

DETAILED DESCRIPTION OF THE INVENTION

The present invention is described in more detail below by way of embodiments and reference to the drawings.

The nucleic acid fragmentation method of the present invention, that is, the method for breaking a nucleic acid into fragments, differs from the prior art in that the method of the present invention is not based on physical disruption or disruption with transposase, but on random annealing of random primers to random sites of the nucleic acid followed by extension reaction to obtain fragmented nucleic acids. The method of the present invention can be used for constructing a nucleic acid library. Therefore, in case where the step of performing PCR amplification is included, the method of the present invention can also be referred to as the method for constructing a nucleic acid library.

Figure 1:
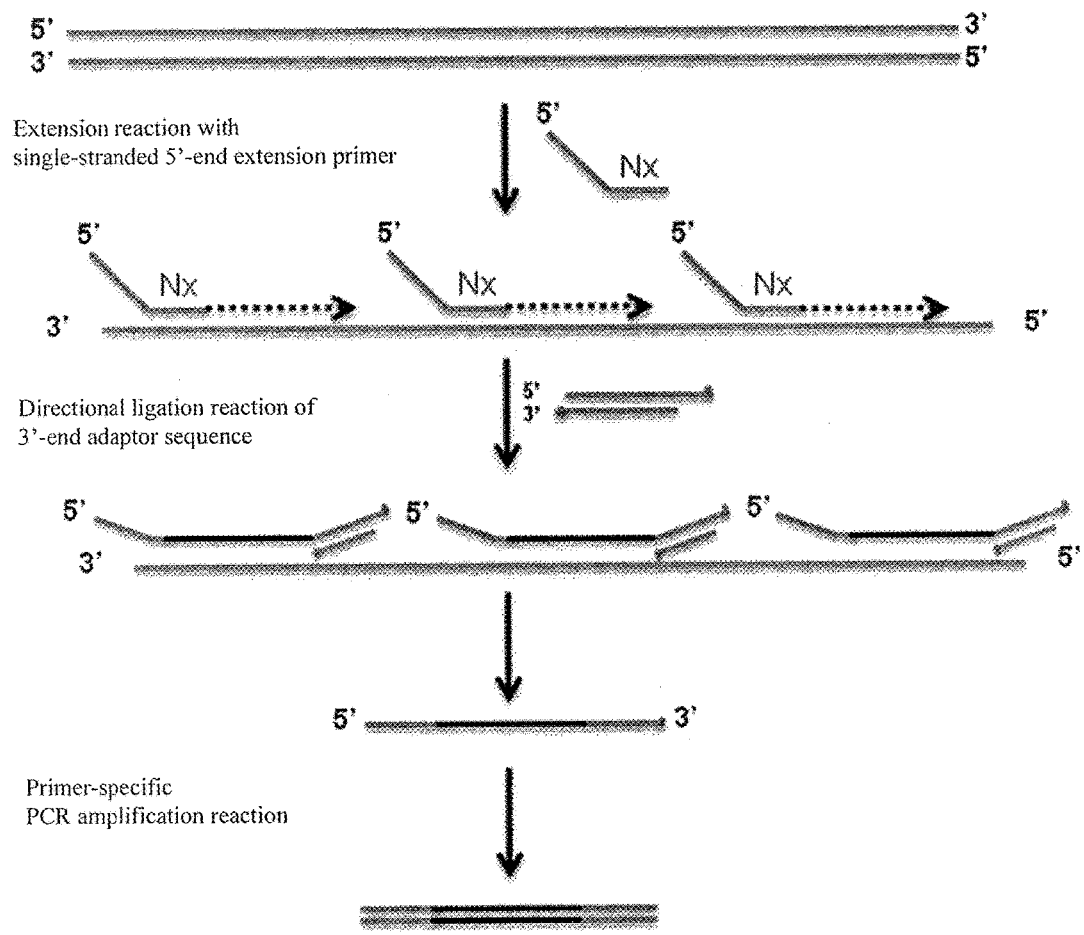
FIG. 1 is a schematic depiction of the procedure of the nucleic acid fragmentation method of the present invention.

Reference is now made to FIG. 1. In an embodiment of the present invention, the nucleic acid fragmentation method includes: (1) subjecting a single-stranded 5'-end extension primer to annealing to a denatured nucleic acid and to have an extension reaction, wherein the single-stranded 5'-end extension primer comprises a sequencing platform adaptor sequence at the 5'-end and a random sequence linked thereto, and the random sequence is subjected to anneal to a random site of the denatured nucleic acid; (2) directionally ligating a double-stranded 3'-end adaptor sequence to the 3'-end of a nucleic acid generated in the extension reaction, following denaturation and purification, a fragmented single-stranded nucleic acid comprising an adaptor sequence at both terminal ends; and (3) generating double-stranded nucleic acid products comprising an adaptor sequence at both terminal ends by primer specific PCR amplification, thus obtaining a nucleic acid library.

The process of step (1) is called controlled primer extension (CPE) reaction, wherein the single-stranded 5'-end extension primer comprises two parts, that is, a sequencing platform adaptor sequence at the 5'-end and a random sequence linked thereto; the random sequence is used for annealing to a random site of the denatured nucleic acid to guide a primer extension reaction, while the sequence platform adaptor sequence is used for subsequent sequencing on a particular sequencing platform; the controlled primer extension reaction achieves random extension with a DNA polymerase, finally obtaining fragmented DNAs comprising the sequencing platform adaptor sequence. The step is called "controlled primer extension reaction" because the carrying out of the primer extension reaction is correlated to the usage amount of the template nucleic acid, the concentration of the extension primer, the concentration of dNTPs, the extension duration, the type and the usage amount of the polymerase, among other factors. Therefore, fragment lengths suitable for a corresponding sequencing platform can be obtained by controlling at least one factor selected from the group consisting of the usage amount of the template nucleic acid, the concentration of the extension primer, the concentration of dNTPs, the extension duration, the type and the usage amount of the polymerase.

The CPE process in step (1) can be specifically divided into three substeps: denaturation, annealing and extension. Denaturation of the double strands of a nucleic acid such as DNA can be achieved by using high temperature treatment method (that is, thermal denaturation) or chemical reagent denaturation method (that is, alkali denaturation). The duration of high temperature treatment is inversely proportional to the temperature, that is, the higher the temperature, the shorter the treatment duration. Suitable denaturation temperatures are in the range of 98-95° C. and a treatment duration of 1-5 minutes. In an embodiment of the present invention, 95° C. and 5 minutes are selected for denaturation. For chemical reagent denaturation method, common denaturing reagents include but not limited to KOH, NaOH and EDTA, among others. If chemical reagent denaturation method is used, then for the annealing reaction to proceed, the alkali ions in the reaction system should be neutralized, such that the reaction system is maintained in a neutral, suitable salt ion environment. If high temperature treatment is used, then the annealing reaction can be achieved by slowly decreasing the temperature. During extension, the types and the usage amounts of dNTPs, the random primer, the DNA polymer etc. and the duration of extension reaction are controlled, such that the size of the extension product fragments meets the need of a sequencing platform.

The DNA polymerase used in the CPE process in step (1) is not specifically limited. In an embodiment of the present invention, primer extension reaction can be successfully achieved by using Klenow Fragment, Taq DNA polymerase, phusion DNA polymerase or E. coli DNA polymerase I. However, different DNA polymerases have different amplification capabilities and amplification rates. Therefore, the type of the DNA polymerase is also a controlling factor in CPE.

Theoretical calculation revealed that the relationship between the usage amount of dNTPs and the usage amount of the template nucleic acid during the CPE process in step (1) is as follows: the usage amount of dNTPs (nmol)= $2*10^{21}*m/Na*5$ to $2*10^{21}*m/Na*5000$, wherein Na represents Avogadro's number, and m represents the usage amount of the template nucleic acid in ng; and the relationship between the usage amount of the extension primer and the usage amount of the template nucleic acid and the length of the extended fragment is as follows: the usage amount of the extension primer (pmol)=$2*10^{24}*m/(N*Na)*5$ to $2*10^{24}*m/(N*Na)*1024$; wherein Na represents Avogadro's number, m represents the usage amount of the template nucleic acid in ng, and N represents the length of the main band of the extended fragment. In Example 1 of the present invention, the range shown in the above formulas was verified. In the above formulas, $2*10^{21}*m/Na$ is a theoretical value, that is, the usage amount of dNTPs (nmol) for m (ng) of DNA covered 1×dNTPs ; and $2*10^{24}*m/(N*Na)$ is a theoretical value of the amount of the primer needed, that is, the theoretical value of the amount of the primer needed (pmol) for m (ng) of DNA to be disrupted into DNA fragments having a main band of N (bp).

The random sequence of the single-stranded 5'-end extension primer is the sequence that anneals to the template DNA single strand, the length thereof generally being in the range of 3-12 nt, preferably 5-8 nt. In an embodiment of the present invention, the random sequence being 5 nt, 6 nt, 7 nt or 8 nt successfully achieves primer extension reaction.

The nucleic acid library constructed by using the nucleic acid fragmentation method of the present invention can be sequenced on a sequencing platform because of the presence of sequencing platform adaptor sequence at both terminal ends. Generally, each sequencing platform has its own particular sequencing platform adaptor sequences. Therefore, the combination of the method of the present invention with the adaptor sequences of different sequencing platforms allows for sequencing on different sequencing platforms. The sequencing platform adaptor sequences include but not limited to the adaptor sequences of Complete Genome (CG), Illumina or Ion Torrent sequencing platform. In the present invention, the adaptor sequences of CG sequencing platform are preferred.

No purification is needed following CPE. By adjusting the concentration of some of the ions in the reaction system, the reaction system can be used in subsequent directional ligation of a double-stranded 3'-end adaptor sequence. Gap ligation occurs between the double-stranded 3'-end adaptor sequence and the extension product bound to the mother chain DNA. In order to avoid self-ligation of the double-stranded 3'-end adaptor sequence which may affect ligation efficiency and PCR amplification reaction in the next step, in an embodiment of the present invention, the length of the double-stranded 3'-end adaptor sequence is specially treated such that one chain is longer than the other chain, and the 3'-terminal end of each chain is subjected to dideoxy modification. The product of directional ligation of the double-stranded 3'-end adaptor sequence is a single-stranded DNA, with both terminal ends having single-stranded adaptors for the sequencing platform. The purification of the single-stranded DNA can be achieved by using single-stranded DNA magnetic bead selection method, the concentration of the magnetic beads being $1.0-1.2\times_o$ In the primer-specific PCR amplification process in step (3), the single-stranded DNA is used as the template, and PCR amplification is mediated by specific primers. One of the primers used comprises a sample tag sequence for tagging a specific sample. That is, for each sample, one of PCR amplification primers has a tag with a specific sequence. In this way, a plurality of samples can be mixed and sequenced together, and then the sequences of the samples can be distinguished according to the sample tag sequences. This can increase sequencing throughput and decrease sequencing cost.

The nucleic acid fragmentation method of the present invention effectively achieves random amplification of a nucleic acid sample by random primer extension procedure, thus obtaining nucleic acid fragments that would be obtained by a conventional disruption method. However, the method of the present invention does not need to use conventional large-scale apparatus and equipment, making it possible for medium and small-sized research institutes, colleges and universities and downstream application sectors to independently conduct high-throughput library preparation. Moreover, the method has the advantages of being simple, convenient, fast, low-cost and highly automatic, which greatly expands the application fields of large-scale high-throughput sequencing. In particular, in the medical and healthcare field relevant to national welfare and the people's livelihood, the method of the present invention gets rid of the dependence on large-scale high-end apparatus and equipment (such as Covaris disruptor), enabling common laboratories in hospitals, universities and research institutes to independently carry out high-throughput library preparation, and increasing timeliness in sample preparation. The method of the present invention is simple and easy to operate, greatly decreasing the requirement for the professional skills of technicians. The whole procedure of library preparation takes a short time, enabling to achieve the fastest sample preparation. The method of the present invention is characterized by a high degree of automation, which can effectively reduce faulty in human operation and decrease systematic error in sample preparation. Moreover, the method of the present invention has the technical advantage of low cost, which lowers the cost in high-throughput gene detection and further expands the fields of application of high-throughput sequencing.

The present invention is illustrated in detail by way of the following specific examples.

EXAMPLE 1

In this example, CPE reactions were conducted using a random primer having 8 random nucletides, various random primer concentrations, various DNA polymerases, various dNTP concentrations, various different DNA starting amounts and various different extension durations, to achieve nucleic acid library construction.

First, genomic DNA was disrupted by CPE, the usage amounts of the primer and dNTPs during CPE being correlated to the usage amount of the genomic DNA. Then, the resulting fragments were directionally ligated with a specially designed 3'-end adaptor, and single-stranded ligation products purified and recovered with magnetic beads were used in primer-specific PCR reaction.

1. A 5'-end random amplification primer comprising 8 random nucletides was designed and synthesized, the sequence of the primer being as follows:

(SEQ ID NO: 1)
GACGACCGCTTGGCCTCCGACTTNNNNNNNN.

The primer was diluted to 1 mM, 100 μM and 10 μM. In this example, the primer used is 10 μM.

2. CPE-denaturation: Genomic DNA used is 50 ng, 100 ng, 150 ng, 200 ng or 1 μg. For a usage amount of 50 ng, the genomic DNA was diluted to 50 ng/μL, and a denaturation reaction solution was established according to Table 1. For other usage amounts, denaturation reaction systems were established accordingly.

TABLE 1

| Component | Usage amount |
| --- | --- |
| DNA | 1 µL |
| ddH$_2$O | 0.6 µL |
| Denaturation buffer (208 mM KOH, 1.3 mM EDTA) | 1 µL |
| Total | 2.6 µL |

The denaturation reaction solution described above was reacting for 3 minutes at room temperature t.

3. CPE-annealing: 1 µL of neutralization buffer (208 mM HCl, 312.5 mM Tris-HCl) was added to the denaturation reaction solution described above, and reaction was at room temperature for 3 minutes. Then, 1 µL of annealing reaction liquid was added, in which, the usage amount of the random primer being between 1.7 to 340 pmol. In this example, the annealing reaction liquid with 1.7 pmol random primer was prepared as follows (Table 2). Annealing reaction liquids having other usage amounts of the random primer were prepared accordingly.

TABLE 2

| Component | Usage amount |
| --- | --- |
| 10 × phi buffer (NEB Corp.) | 0.46 µL |
| ddH$_2$O | 0.37 µL |
| Random primer (10 µM) | 0.17 µL |
| Total | 1 µL |

The annealing reaction solution described above was reacting for 10 minutes at room temperature.

4. CPE-extension: 15.4 µL of extension reaction liquid was added to the annealing reaction solution described above, the amount of the dNTPs in the extension reaction liquid being between 0.85 to 850 nmol. In this example, the extension reaction liquid having 0.85 nmol dNTPs was prepared as follows (Table 3). Extension reaction liquids having other usage amounts of the dNTPs were prepared accordingly. In this example, Taq DNA polymerase, phusion DNA polymerase and *E. Coli* DNA polymerase I were also used in the extension reaction besides Klenow Fragment.

TABLE 3

| Component | Usage amount |
| --- | --- |
| 10 × phi buffer (NEB Corp.) | 1.54 µL |
| Pure water | 3.76 µL |
| Dimethyl sulfoxide | 1 µL |
| Betaine (5M) | 8 µL |
| dNTPs (0.25 mM each) | 0.85 µL |
| Klenow Fragment | 0.25 µL |
| Total | 15.4 µL |

The conditions for extension (temperature and duration) were correlated to the size of the library suitable for a sequencing platform. In this example, extension at 37° C. for 5 to 30 minutes was employed. Then, reaction at 65° C. for 15 minutes was conducted to thermally inactivate the DNA polymerase.

5. Adaptor ligation:

3'-end adaptor sequences as follows (sequence A and sequence B) were designed and synthesized:

Sequence A: GCTTCGACTGGAGA ddC (SEQ ID NO: 2, wherein dd represents 3'-end dideoxy modification);

Sequence B: pGTCTCCAGTCGAAGCCCGACG ddC (SEQ ID NO: 3, wherein dd represents 3'-end dideoxy modification, and p represents 5'-end phosphorylation modification).

Sequence A and sequence B were respectively diluted to 100 µM and mixed in equal ratio followed by centrifugation. Annealing was allowed in a PCR instrument according to the following procedure (Table 4) to obtain the 3'-end adaptor. The adaptor was diluted to 5 µM for later use.

TABLE 4

| Temperature | Duration |
| --- | --- |
| 75° C. | 15 min |
| 60° C. | 10 min |
| 50° C. | 10 min |
| 40° C. | 10 min |
| 25° C. | 30 min |
| Hot cover 105° C. | |

Then, a ligation reaction solution was established according to the following Table 5:

TABLE 5

| Component | Usage amount |
| --- | --- |
| CPE reaction product | 15 µL |
| Ligation buffer | 10 µL |
| T4 DNA ligase | 1 µL |
| 3'-end adaptor (5 µM) | 4 µL |
| Total | 30 µL |

The reaction tubes containing the above-said ligation reaction solution were placed in a PCR instrument to react at 25° C. for 1.5 hours and then at 65° C. for 10 minutes.

6. Purifying ligation products: Before purification, the ligation products were denatured for 5 minutes at 95° C.-98° C. Single-stranded ligation products were purified using magnetic bead method. 1.0-1.2×PEG32 magnetic beads (CG brand, Art. No. MP07123) could be used. In this example, 1.0×PEG32 magnetic beads were selected. That is, 30 µL of PEG32 magnetic beads were added into 30 µL ligation solution described above to purify the single-stranded ligation products, which were then redissolved in pure water.

7. PCR reaction: the ligation products were subjected to specific primer amplification, the PCR primers being designed as follows (F primer and R primer):

```
F Primer:
                                      (SEQ ID NO: 4)
TCCTAAGACCGCTTGGCCTCCGACT;

R primer:
                                      (SEQ ID NO: 5)
AGACAAGCTCNNNNNNNNNNNNGATCGGGCTTCGACTGGAGAC.
```

The R primer comprises a sample tag sequence, that is, a barcode sequence (underlined portion), which is useful for discriminating sequence information of different samples mixed and sequenced together.

PCR amplification reaction was conducted according to the following PCR reaction solution (Table 6) and reaction conditions (Table 7).

TABLE 6

| Component | Usage amount |
| --- | --- |
| Ligation product | 20.5 μL |
| single-stranded DNA | |
| 2 × PCR buffer (containing Mg$^{2+}$) | 25 μL |
| F primer (20 μM) | 2 μL |
| R primer (20 μM) | 2 μL |
| PCR enzyme | 0.5 μL |
| Total | 50 μL |

TABLE 7

| Temperature | Duration | Cycles |
| --- | --- | --- |
| 95° C. | 3 min | 1 |
| 95° C. | 30 sec | 15 |
| 55° C. | 30 sec | |
| 72° C. | 1 min | |
| 72° C. | 10 min | 1 |
| 4° C. | ∞ | — |

Figure 2:
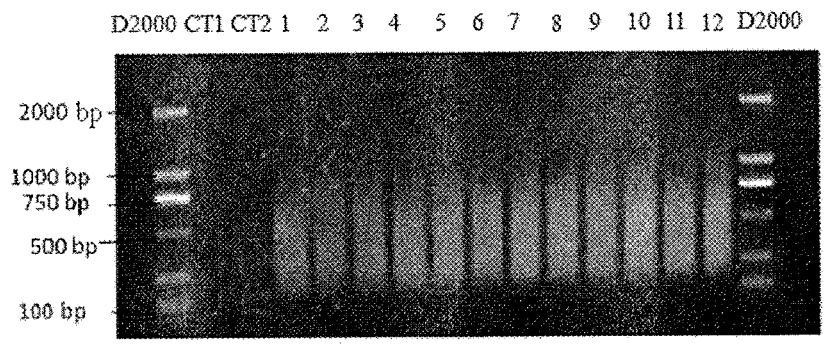
FIG. 2 is the results of gel electrophoretic detection of the DNA library prepared in Example 1 of the present invention, in which: D2000 represents DNA Marker; CT1 represents No. 1 control in which DNA is denatured but not subjected to neutralization reaction; CT2 represents No. 2 control which is PCR negative control; 1: 50 ng DNA starting amount, extension primer 1.7 pmol, dNTP 0.85 nmol, extension at 37° C. for 5 min, Klenow Fragment; 2: 50 ng DNA starting amount, extension primer 1.7 pmol, dNTP 850 nmol, extension at 37° C. for 5 min, Klenow Fragment; 3: 50 ng DNA starting amount, extension primer 340 pmol, dNTP 0.85 nmol, extension at 37° C. for 5 min, Klenow Fragment; 4: 50 ng DNA starting amount, extension primer 340 pmol, dNTP 850 nmol, extension at 37° C. for 5 min, Klenow Fragment; 5: 50 ng DNA starting amount, extension primer 1.7 pmol, dNTP 0.85 nmol, extension at 37° C. for 30 min, Klenow Fragment; 6: 50 ng DNA starting amount, extension primer 1.7 pmol, dNTP 0.85 nmol, extension at 37° C. for 5 min, Taq DNA polymerase; 7: 50 ng DNA starting amount, extension primer 1.7 pmol, dNTP 0.85 nmol, extension at 37° C. for 5 min, phusion DNA polymerase; 8: 50 ng DNA starting amount, extension primer 1.7 pmol, dNTP 0.85 nmol, extension at 37° C. for 5 min, *E. Coli* DNA polymerase I; 9: 100 ng DNA starting amount, extension primer 3.4 pmol, dNTP 1.7 nmol, extension at 37° C. for 5 min, Klenow Fragment; 10: 150 ng DNA starting amount, extension primer 5.1 pmol, dNTP 2.55 nmol, extension at 37° C. for 5 min, Klenow Fragment; 11: 200 ng DNA starting amount, extension primer 6.8 pmol, dNTP 3.4 nmol, extension at 37° C. for 5 min, Klenow Fragment; and 12: 1μg DNA starting amount, extension primer 34 pmol, dNTP 17 nmol, extension at 37° C. for 5 min, Klenow Fragment.

8. The products of the above PCR were subjected to gel agarose electrophoresis detection, and the results was shown in FIG. 2. The results indicated that discrete PCR products were obtained for each experiment, suggesting that nucleic acid library construction could be successfully achieved by conducting CPE reaction using various random primer concentrations, various DNA polymerases, various dNTP concentrations, various different DNA starting amounts and various different extension durations.

EXAMPLE 2

This example was conducted under the same conditions as those in the above Tables 1-7 for Example 1, except that CPE reaction was conducted using random primers having 5, 6 and 7 random nucleotides respectively.

The sequences of the random primers were as follows:

```
                                          (SEQ ID NO: 6)
GACGACCGCTTGGCCTCCGACTTNNNNNNN;

(SEQ ID NO: 7)
GACGACCGCTTGGCCTCCGACTTNNNNNN;

(SEQ ID NO: 8)
GACGACCGCTTGGCCTCCGACTTNNNNN.
```

Figure 3:
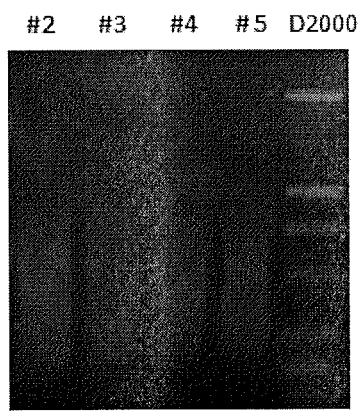
FIG. 3 is the results of gel electrophoretic detection of the DNA library prepared in Example 2 of the present invention, in which D2000 represents DNA Marker; #2: 8 random nucletides; #3: 7 random nucletides; #4: 6 random nucletides; and #5: 5 random nucletides.

The PCR products finally obtained were subjected to gel agarose electrophoresis detection, the results being as shown in FIG. 3. The results indicated that discrete PCR products were obtained for each experiment group, suggesting that nucleic acid library construction could be successfully achieved by conducting CPE reaction using random primers having 5-8 random nucleotides.

EXAMPLE 3

This example was conducted under the same conditions as those in the above Tables 1-7 for Example 1, except that the denaturation step was conducted by reacting at 95° C. for 5 minutes instead of KOH denaturation in Example 1, which accordingly eliminates the need of the neutralization reaction.

Figure 4:
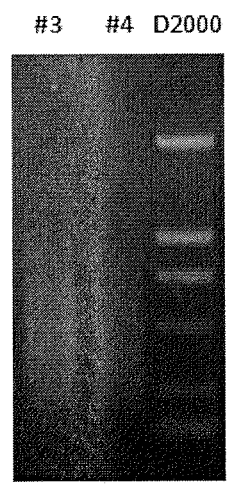
FIG. 4 is the results of gel electrophoretic detection of the DNA library prepared in Example 3 of the present invention, in which D2000 represents DNA Marker; #3: DNA denaturation is achieved by treatment with KOH+EDTA denaturation buffer (Example 1); and #4: DNA denaturation is achieved by reaction at 95° C. for 5 minutes.

The PCR products finally obtained were subjected to gel agarose electrophoresis detection, the results being as shown in FIG. 4. The results indicated that discrete PCR products were obtained for each experiment group, suggesting that nucleic acid library construction could be successfully achieved by conducting CPE reaction following denaturation by reacting at 95° C. for 5 minutes.

EXAMPLE 4

In this example, an amount of 50 ng of genomic DNA was used to conduct CPE reaction with a random primer comprising 8 random nucleotides which is suitable for use on an Illumina sequencing platform, then 3'-adaptor ligation was conducted using a modified double-stranded adaptor suitable for use on a Illumina platform, and PCR amplification was conducted using PCR specific primers appropriate for the adaptor to obtain a DNA library that can be used on an Illumina platform to perform genomic sequencing.

1. A 5'-end random amplification primer comprising 8 random nucleotides was designed and synthesized, the sequence being as follows:

```
                                          (SEQ ID NO: 9)
TACACTCTTTCCCTACACGACGCTCTTCCGATCNNNNNNNN.
```

In this example, the primer was used at 10 μM.

2. CPE-denaturation: In this example, genomic DNA was used at an amount of 50 ng. The genomic DNA was diluted to 50 ng/μL, and a denaturation reaction solution was established according to the following system (Table 8).

TABLE 8

| Component | Usage amount |
| --- | --- |
| DNA | 1 μL |
| ddH$_2$O | 0.6 μL |
| Denaturation buffer (208 mM KOH, 1.3 mM EDTA) | 1 μL |
| Total | 2.6 μL |

The denaturation reaction solution described above was reacting 3 minutes at room temperature.

3. CPE-annealing: 1 μL of neutralization buffer (208 mM HCl, 312.5 mM Tris-HCl) was added to the denaturation reaction solution described above, and reaction was allowed at room temperature for 3 minutes. Then, 1 μL of annealing reaction liquid was added, the usage amount of the random primer was 1.7 pmol. The annealing reaction liquid was prepared as follows (Table 9).

TABLE 9

| Component | Usage amount |
| --- | --- |
| 10 × phi buffer (NEB Corp.) | 0.46 μL |
| ddH$_2$O | 0.37 μL |
| Random primer (10 μM) | 0.17 μL |
| Total | 1 μL |

The annealing reaction solution described above was reacting for 10 minutes at room temperature.

4. CPE-extension: 15.4 μL of extension reaction liquid was added to the annealing reaction solution described above, the amount of the dNTPs in the extension reaction liquid being 0.85 nmol. The extension reaction liquid was prepared as follows (Table 10). In this example, Klenow Fragment was used to conduct extension reaction.

TABLE 10

| Component | Usage amount |
| --- | --- |
| 10 × phi buffer (NEB Corp.) | 1.54 μL |
| Pure water | 3.76 μL |
| Dimethyl sulfoxide | 1 μL |
| Betaine (5M) | 8 μL |
| dNTPs (0.25 mM each) | 0.85 μL |
| Klenow Fragment | 0.25 μL |
| Total | 15.4 μL |

The conditions for extension (temperature and duration) were correlated to the size of the library suitable for a sequencing platform. In this example, extension at 37° C. for 5-30 minutes was employed. Then, reaction at 65° C. for 15 minutes was conducted to thermally inactivate the DNA polymerase.

5. Adaptor ligation:

3'-end adaptor sequences as follows (sequence A and sequence B) were designed and synthesized:

Sequence A: GCTCTTCCGAT ddC (SEQ ID NO: 10, wherein dd represents 3'-end dideoxy modification);

Sequence B: pGATCGGAAGAGCACACGTCTGAACTCCAGTCA ddC (SEQ ID NO: 11, wherein dd represents 3'-end dideoxy modification, and p represents 5'-end phosphorylation modification).

Sequence A and sequence B were respectively diluted to 100 μM and mixed in equal ratio followed by centrifugation. Annealing was allowed in a PCR instrument according to the following procedure (Table 11) to obtain the 3'-end adaptor. The adaptor was diluted to 5 μM for later use.

TABLE 11

| Temperature | Duration |
| --- | --- |
| 75° C. | 15 min |
| 60° C. | 10 min |
| 50° C. | 10 min |
| 40° C. | 10 min |
| 25° C. | 30 min |
| Hot cover 105° C. | |

Then, a ligation reaction solution was established according to the following system (Table 12):

TABLE 12

| Component | Usage amount |
| --- | --- |
| CPE reaction product | 15 μL |
| Ligation buffer | 10 μL |
| T4 DNA ligase | 1 μL |
| 3'-end adaptor (5 μM) | 4 μL |
| Total | 30 μL |

The reaction tubes containing the above-said ligation reaction solution were placed in a PCR instrument to allow reaction at 25° C. for 1.5 hours and then at 65° C. for 10 minutes.

6. Purifying ligation products: Before purification, the ligation products were denatured at 95° C.-98° C. for 5 minutes. Single-stranded ligation products were purified using magnetic bead method. 1.0-1.2×PEG32 magnetic beads could be used. In this example, 1.0×PEG32 magnetic beads were selected. That is, 30 μL of PEG32 magnetic beads were added into 30 μL of the ligation solution described above to purify the single-stranded ligation products, which were then redissolved in pure water.

7. PCR reaction: the ligation products were subjected to specific primer amplification, and the PCR primers were designed as follows (F primer and R primer):

F primer:
(SEQ ID NO: 12)
AATGATACGGCGACCACCGAGATCTACACTCTTTCCCTACACGACGC
TCTTCCGATCT;

R primer:
(SEQ ID NO: 13)
CAAGCAGAAGACGGCATACGAGATANNNNNNNNNTGACTGGAGTTCAG
ACGTGTGCTCTTCCGATCT.

The R primer comprises a sample tag sequence, that is, a barcode (underlined portion), which is useful for discriminating sequence information of different samples after mixing and sequencing.

PCR amplification reaction was conducted according to the following PCR reaction solution (Table 13) and reaction conditions (Table 14).

TABLE 13

| Component | Usage amount |
| --- | --- |
| Ligation product single-stranded DNA | 20.5 μL |
| 2 × PCR buffer (containing $Mg^{2+}$) | 25 μL |
| F primer (20 μM) | 2 μL |
| R primer (20 μM) | 2 μL |
| PCR enzyme | 0.5 μL |
| Total | 50 μL |

TABLE 14

| Temperature | Duration | Cycles |
| --- | --- | --- |
| 95° C. | 3 min | 1 |
| 95° C. | 30 sec | 15 |
| 62° C. | 30 sec | |
| 72° C. | 1 min | |
| 72° C. | 10 min | 1 |
| 4° C. | ∞ | — |

Figure 5:
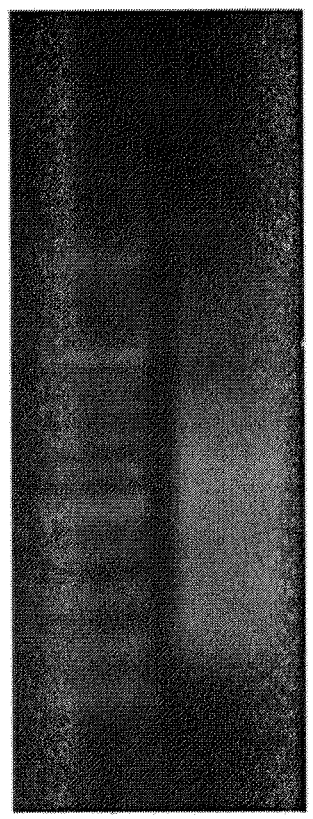
FIG. 5 is the results of gel electrophoretic detection of the DNA library prepared in Example 4 of the present invention, in which M represents 100 bp DNA Marker; #1 represents DNA library products obtained by PCR amplification.

8. The products of the above PCR were detected by gel agarose electrophoresis, the results being as shown in FIG. 5. The results indicated that DNA library products discretely distributed between 200-800 bp, which met the requirements of Illumina sequencing platform.

9. The above library was quality checked to be up to standard, and was designated as HUMkrbDR500-13. The library was sequenced and the sequencing type was PE101+8+101.

10. The basic information of the raw data is summarized as follows (Table 15).

TABLE 15

| HUMkrbDR500-13 | |
| --- | --- |
| Parameter | Result |
| Raw reads | 8112981 |
| Read1_Q20 | 89.6 |
| Read2_Q20 | 85.6 |
| Read1_GC | 49 |
| Read2_GC | 49.2 |

TABLE 15-continued

| HUMkrbDR500-13 | |
| --- | --- |
| Parameter | Result |
| Low quality reads | 615308 |
| Duplicate reads | 219420 |
| Duplication_percent | 2.70% |

Note:
Read1 and Read2 respectively represent the reads generated from double-end sequencing on an Illumina platform, and Q20 refers to reads with an error rate of 1%.

11. The degree of coverage was analyzed as follows:

4620283 high quality reads (clean reads, that is, those reads free of low quality and adaptor contamination, among others) were obtained from the HUMkrbDR500-13 library to analyze the degree of coverage, the results being as shown in Table 16.

TABLE 16

| HUMkrbDR500-13 | |
| --- | --- |
| Parameter | Result |
| Genome_coverage (that is, the percentage of the sequencing reads covering the genome) | 99.90% |
| Genome_coverage_4× (a degree of genome coverage achieving 4-fold covering, that is, the | 99.14% |

TABLE 16-continued

| HUMkrbDR500-13 | |
| --- | --- |
| Parameter | Result |
| percentage of the sequencing reads covering the genome 4-fold) | |
| Genome_coverage_10× | 96.89% |
| Genome_coverage_20× | 91.20% |
| Genome_coverage_30× | 83.09% |
| Genome_coverage_40× | 73.23% |
| Genome_coverage_50× | 62.85% |

Figure 6:
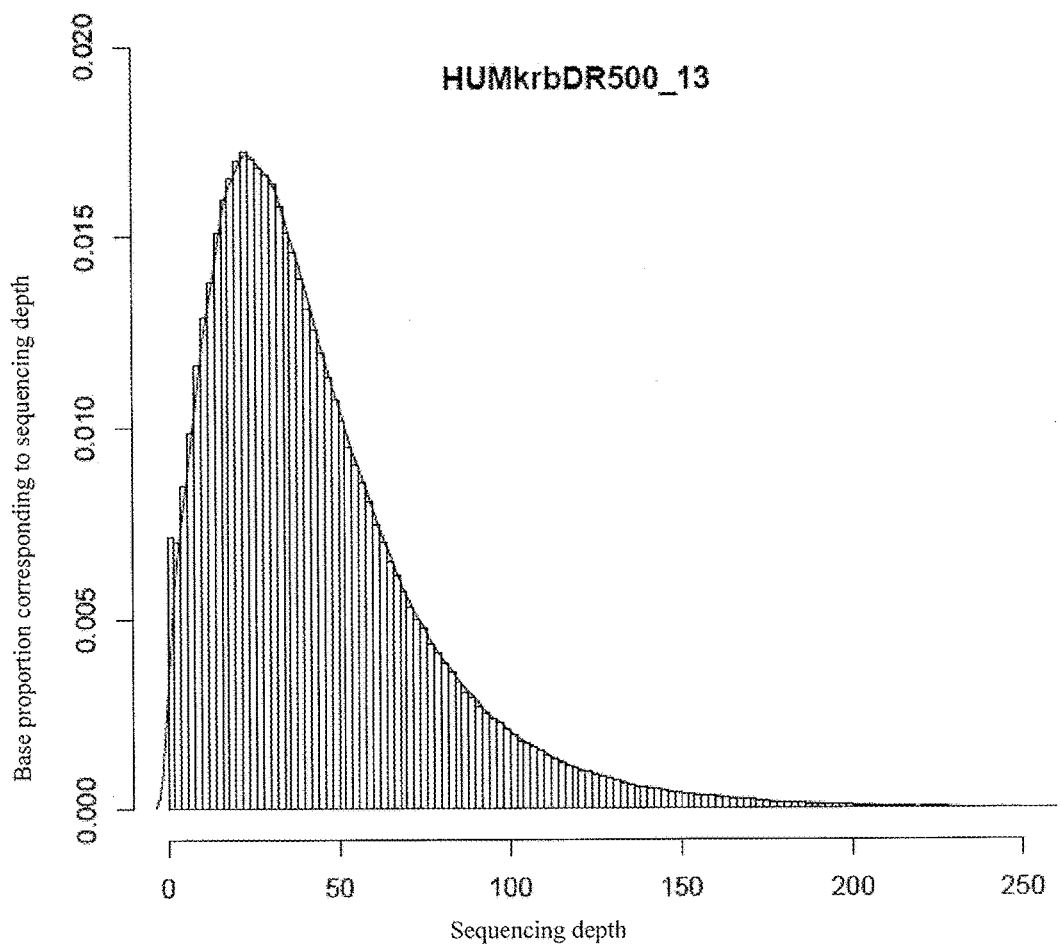
FIG. 6 is a statistical graph of the coverage depth obtained by sequencing the DNA library prepared in Example 4 of the present invention on an Illumina sequencing platform.
Figure 7:
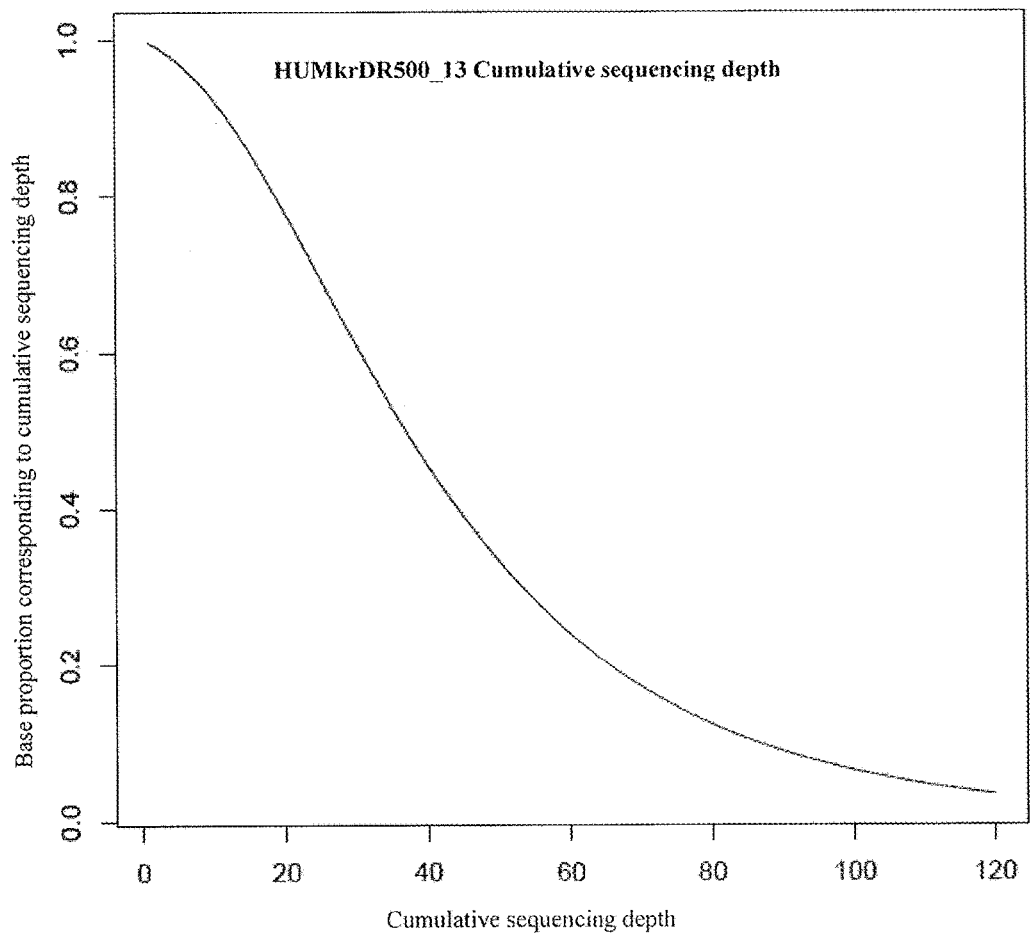
FIG. 7 is a statistical graph of the cumulative coverage depth obtained by sequencing the DNA library prepared in Example 4 of the present invention on an Illumina sequencing platform.

The result of coverage depth statistics is as shown in FIG. 6, and the result of cumulative coverage depth statistics is as shown in FIG. 7.

Figure 8:
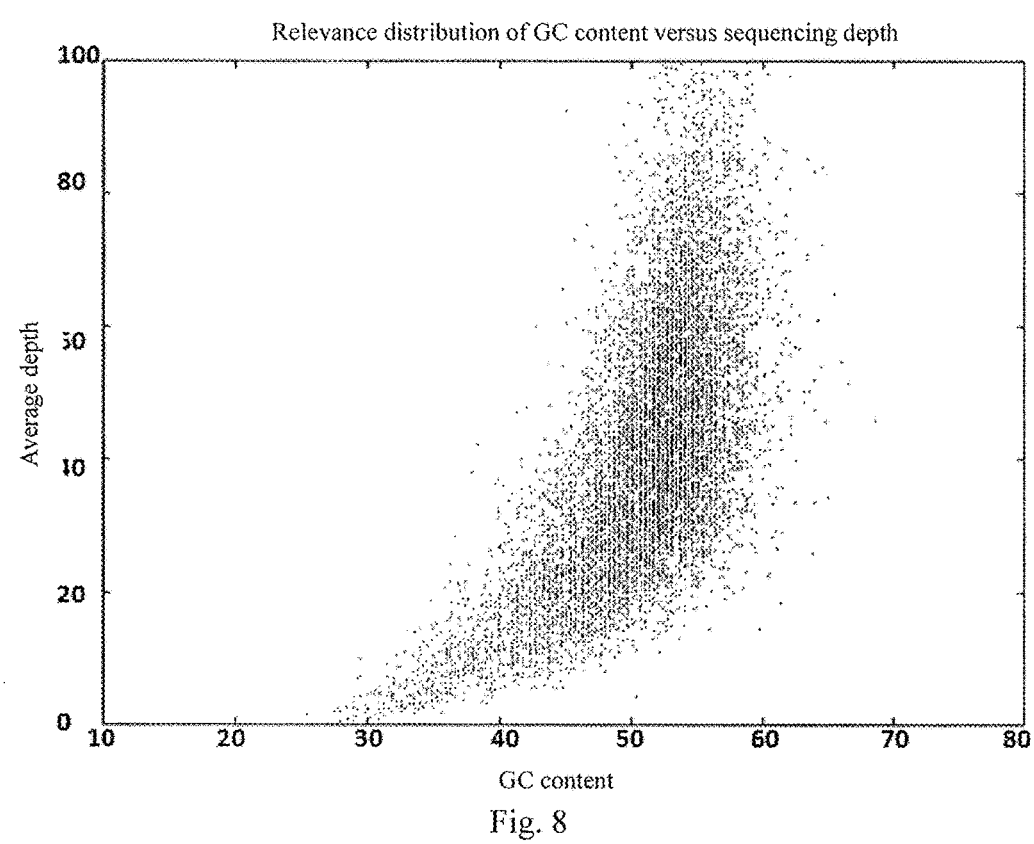
FIG. 8 is a graph showing the result of randomness analysis of the sequencing depth, obtained by sequencing the DNA library prepared in Example 4 of the present invention on an Illumina sequencing platform, versus GC content.

12. Analysis of randomness was conducted as follows:

4620283 clean reads were obtained from the HUMkrbDR500-13 library to analyze the randomness, the result of randomness analysis being as shown in FIG. 8. The randomness exhibited a slight bias towards GC, with the GC-rich regions having a slightly deeper coverage depth.

The disclosure set forth hereinabove has described the present invention in further detail by way of could embodiments and examples, and is not to be construed as limiting the particular implementations of the present invention thereto. A number of simple deductions or substitutions be made by a person of common skill in the art without departing from the concept of the present invention.

We claim:

1. A method of producing nucleic acid fragments, wherein the method comprises the following steps:

subjecting a single-stranded 5'-end extension primer to anneal to a denatured nucleic acid and to have an extension reaction, wherein the single-stranded 5'-end extension primer comprises a sequencing platform adaptor sequence at the 5'-end and a random sequence linked thereto, and the random sequence is subjected to anneal to a random site of the denatured nucleic acid; and directionally ligating a double-stranded 3'-end adaptor sequence to the 3'-end of the nucleic acid generated in the extension reaction, and then performing denaturation and purification to obtain fragmented single-stranded nucleic acids comprising an adaptor sequence at both terminal ends, wherein the ligating occurs between the double-stranded 3'-end adaptor sequence and the extension product bound to the denatured nucleic acid.

2. The method according to claim 1, wherein after ligating the double-stranded 3'-end adaptor sequence, primer-specific PCR amplification is conducted to generate double-stranded nucleic acid products comprising an adaptor sequence at both terminal ends.

3. The method according to claim 1, wherein the random sequence has a length of 3 to 12 nt.

4. The method according to claim 1, wherein the denaturation is alkali denaturation or thermal denaturation.

5. The method according to claim 1, wherein the 5'-end sequencing platform adaptor sequence and the double-stranded 3'-end adaptor sequence are selected from the adaptor sequences available for CG, Illumina or Ion Torrent sequencing platforms.

6. The method according to claim 1, wherein in the annealing and extension reaction step of the method, at least one factor selected from the group consisting of the usage amount of the denatured nucleic acid, the concentration of the extension primer, the concentrations of dNTPs, the extension duration, and the type and the usage amount of polymerase is controlled to obtain suitable fragment lengths for a corresponding sequencing platform.

7. The method according to claim 6, wherein the usage amount of the denatured nucleic acid is between 50 to 1000 ng.

8. The method according to claim 6, wherein the extension duration is between 5 to 30 minutes.

9. The method according to claim 6, wherein the polymerase is selected from the group consisting of Klenow Fragment, Taq DNA polymerase, phusion DNA polymerase and *E. coli* DNA polymerase I.

10. The method according to claim 6, wherein the relationship between the usage amount of dNTPs and the usage amount of the denatured nucleic acid is as follows: the usage amount of dNTPs (nmol)=$2*10^{21}*m/Na*5$ to $2*10^{21}*m/Na*5000$, wherein Na represents Avogadro's number, and m represents the usage amount of the denatured nucleic acid in ng.

11. The method according to claim 6, wherein the relationship between the usage amount of the extension primer and the usage amount of the denatured nucleic acid and the length of the extended fragment is as follows: the usage amount of the extension primer (pmol)=$2*10^{24}*m/(N*Na)*5$ to $2*10^{24}*m/(N*Na)*1024$; wherein Na represents Avogadro's number, m represents the usage amount of the denatured nucleic acid in ng, and N represents the length of a main band of the extended fragments.

12. The method according to claim 2, wherein the 3'-end of each single strand of the double-stranded 3'-end adaptor sequence is a nucleotide with dideoxy modification.

13. The method according to claim 2, wherein one of the primers used in the primer-specific PCR amplification comprises a sample tag sequence.

14. A sequence combination for producing nucleic acid fragments, wherein the sequence combination comprises:

a single-stranded 5'-end extension primer, comprising a sequencing platform adaptor sequence at the 5'-end and a random sequence linked thereto, wherein the random sequence is to be subjected to anneal to a random site of a denatured nucleic acid and to have an extension reaction; and a double-stranded 3'-end adaptor sequence, wherein the double-stranded 3'-end adaptor sequence comprises two chains, and the 3'-terminal end of each chain is subjected to modification to avoid self-ligation of the double-stranded 3'-end adaptor sequence, the double-stranded 3'-end adaptor sequence is to be directionally ligated to the 3'-end of the nucleic acid generated in the extension reaction, following denaturation and purification, fragmented single-stranded nucleic acids comprising an adaptor sequence at both terminal ends are generated.

15. The sequence combination according to claim 14, wherein the random sequence has a length of 3 to 12 nt.

16. The sequence combination according to claim 14, wherein the 5'-end sequencing platform adaptor sequence and the double-stranded 3'-end adaptor sequence are selected from the adaptor sequences available for CG, Illumina or Ion Torrent sequencing platforms.

17. The method according to claim 4, wherein the alkali denaturation is conducted by treatment with a NaOH or KOH solution.

18. The method according to claim 4, wherein the thermal denaturation is conducted at a temperature of 95° C. to 98° C.

* * * * *

SEQUENCE LISTING

```
<160> NUMBER OF SEQ ID NOS: 13

<210> SEQ ID NO 1
<211> LENGTH: 31
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (24)..(31)
<223> OTHER INFORMATION: n is a, c, g, or t

<400> SEQUENCE: 1
gacgaccgct tggcctccga cttnnnnnnn n                                  31

<210> SEQ ID NO 2
<211> LENGTH: 15
<212> TYPE: DNA
<213> ORGANISM: Artificial Sequence
<220> FEATURE:
<223> OTHER INFORMATION: Synthetic Sequence
<220> FEATURE:
<221> NAME/KEY: 3'-end dideoxy modification
<222> LOCATION: (15)..(15)

<400> SEQUENCE: 2
gcttcgactg gagac                                                    15

<210> SEQ ID NO 3
<211> LENGTH: 22
<212> TYPE: DNA
<213> ORGANISM: Artificial Sequence
<220> FEATURE:
<223> OTHER INFORMATION: Synthetic Sequence
<220> FEATURE:
<221> NAME/KEY: 5'-end phosphorylation modification
<222> LOCATION: (1)..(1)
<220> FEATURE:
```

```
<221> NAME/KEY: 3'-end dideoxy modification
<222> LOCATION: (22)..(22)

<400> SEQUENCE: 3
gtctccagtc gaagcccgac gc                                              22

<210> SEQ ID NO 4
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 4
tcctaagacc gcttggcctc cgact                                           25

<210> SEQ ID NO 5
<211> LENGTH: 41
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (11)..(20)
<223> OTHER INFORMATION: n is a, c, g, or t

<400> SEQUENCE: 5
agacaagctc nnnnnnnnnn gatcgggctt cgactggaga c                         41

<210> SEQ ID NO 6
<211> LENGTH: 30
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (24)..(30)
<223> OTHER INFORMATION: n is a, c, g, or t

<400> SEQUENCE: 6
gacgaccgct tggcctccga cttnnnnnnn                                      30

<210> SEQ ID NO 7
<211> LENGTH: 29
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (24)..(29)
<223> OTHER INFORMATION: n is a, c, g, or t

<400> SEQUENCE: 7
gacgaccgct tggcctccga cttnnnnnn                                       29

<210> SEQ ID NO 8
<211> LENGTH: 28
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (24)..(28)
<223> OTHER INFORMATION: n is a, c, g, or t
```

```
<400> SEQUENCE: 8
gacgaccgct tggcctccga cttnnnnn                                              28

<210> SEQ ID NO 9
<211> LENGTH: 41
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (34)..(41)
<223> OTHER INFORMATION: n is a, c, g, or t

<400> SEQUENCE: 9
tacactcttt ccctacacga cgctcttccg atcnnnnnnn n                               41

<210> SEQ ID NO 10
<211> LENGTH: 12
<212> TYPE: DNA
<213> ORGANISM: Artificial Sequence
<220> FEATURE:
<223> OTHER INFORMATION: Synthetic Sequence
<220> FEATURE:
<221> NAME/KEY: 3'-end dideoxy modification
<222> LOCATION: (12)..(12)

<400> SEQUENCE: 10
gctcttccga tc                                                               12

<210> SEQ ID NO 11
<211> LENGTH: 33
<212> TYPE: DNA
<213> ORGANISM: Artificial Sequence
<220> FEATURE:
<223> OTHER INFORMATION: Synthetic Sequence
<220> FEATURE:
<221> NAME/KEY: 5'-end phosphorylation modification
<222> LOCATION: (1)..(1)
<220> FEATURE:
<221> NAME/KEY: 3'-end dideoxy modification
<222> LOCATION: (33)..(33)

<400> SEQUENCE: 11
gatcggaaga gcacacgtct gaactccagt cac                                        33

<210> SEQ ID NO 12
<211> LENGTH: 58
<212> TYPE: DNA
<213> ORGANISM: Artificial Sequence
<220> FEATURE:
<223> OTHER INFORMATION: Synthetic Sequence

<400> SEQUENCE: 12
aatgatacgg cgaccaccga gatctacact ctttccctac acgacgctct tccgatct            58

<210> SEQ ID NO 13
<211> LENGTH: 66
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (26)..(33)
<223> OTHER INFORMATION: n is a, c, g, or t

<400> SEQUENCE: 13
```

```
caagcagaag acggcatacg agatannnnn nnntgactgg agttcagacg tgtgctcttc      60
cgatct                                                                66
```